US012797622B2

(12) United States Patent
Villamil et al.

(10) Patent No.: US 12,797,622 B2
(45) Date of Patent: Nov. 17, 2026

(54) STRAIN-RELIEF/LEAD ASSEMBLY ELECTRICALLY AND MECHANICALLY CONNECTED TO AN ACTIVE MEDICAL DEVICE

(71) Applicant: Greatbatch Ltd., Clarence, NY (US)

(72) Inventors: Luis Daniel Villamil, Montevideo (UY); Ignacio Agustin Armesto, Montevideo (UY); Hugh D. Hestad, Edina, MN (US)

(73) Assignee: Greatbatch Ltd., Clarence, NY (US)

( * ) Notice: Subject to any disclaimer, the term of this patent is extended or adjusted under 35 U.S.C. 154(b) by 311 days.

(21) Appl. No.: 18/658,314

(22) Filed: May 8, 2024

(65) Prior Publication Data

US 2024/0374905 A1 Nov. 14, 2024

Related U.S. Application Data

(60) Provisional application No. 63/465,901, filed on May 12, 2023.

(51) Int. Cl.
*A61N 1/375* (2006.01)

(52) U.S. Cl.
CPC .................................. *A61N 1/3754* (2013.01)

(58) Field of Classification Search
None
See application file for complete search history.

(56) References Cited

U.S. PATENT DOCUMENTS

| | | | | |
|---|---|---|---|---|
| 7,590,451 | B2 * | 9/2009 | Tronnes | A61N 1/3752 607/37 |
| 7,794,256 | B1 | 9/2010 | Sochor | |
| 8,162,684 | B1 * | 4/2012 | Sochor | H01R 13/639 439/289 |
| 9,011,169 | B2 | 4/2015 | Russell et al. | |
| 9,673,558 | B2 * | 6/2017 | Frey | H01R 13/512 |
| 2004/0106964 | A1 | 6/2004 | Fischer et al. | |

* cited by examiner

*Primary Examiner* — Tho D Ta
(74) *Attorney, Agent, or Firm* — Hodgson Russ LLP

(57) ABSTRACT

An active medical device has a feedthrough comprising a ferrule sealed to a ceramic insulator supporting a short terminal pin and a long terminal pin that are connected to electronic components in the device housing. A silicone insulator residing in the ferrule abutting the ceramic insulator has first and second openings that house first and second metallic housings nesting respective coil springs. The metallic housings connected to the respective short and long terminal pins are axially aligned in the silicon insulator. A lead connector connected to a strain-relief for a lead supports a co-axial lead pin having electrically isolated center and circumferential outer conductors. When the lead connector/strain-relief subassembly is connected to the feedthrough, the center and circumferential conductors of the lead pin are electrically connected to the coil springs nested in the first and second metallic housings connected to the short and long terminal pins of the feedthrough.

20 Claims, 7 Drawing Sheets

STRAIN-RELIEF/LEAD ASSEMBLY ELECTRICALLY AND MECHANICALLY CONNECTED TO AN ACTIVE MEDICAL DEVICE

CROSS-REFERENCE TO RELATED APPLICATION

This application claims priority to U.S. provisional application Ser. No. 63/465,901, filed on May 12, 2023.

BACKGROUND OF THE INVENTION

1. Field of the Invention

The present invention relates to the field of implantable medical devices. More particularly, the present invention relates to a miniature-sized active medical device (AMD) that is designed to deliver electrical stimulation to a patient or sense biological signals from body tissue. A miniature-sized AMD is defined as a medical device that has a volume of less than about 3 cc. The AMD can be implanted in a patient's body or worn externally on the body.

The desire to make AMDs as small as possible is an active area of innovation. Implanting a miniature-sized AMD is advantageous over implanting a conventionally-sized pulse generator for many reasons. Chief among them is that the implantation procedure can be performed with far less surgical trauma to the patient. As long as the miniature AMD has the same or similar functionality as an AMD of a conventional size, subjecting the patient to less trauma represents an advancement in the industry. This includes implanting a miniature-sized neurostimulator for pain therapy. Additionally, a miniature-sized neurostimulator can be applied to many more nerves, particularly to smaller nerves, than a relatively larger, conventionally-sized AMD. Further, an externally worm miniature AMD would be expected to be less bothersome to a patient than a larger version of the same device.

2. Prior Art

A conventional active medical device (AMD) has a molded header assembly containing a row of co-axially aligned terminal blocks that are electrically insulated from each other. Each terminal block is connected to the body fluid side of a terminal pin that extends through a hermetic glass-to-metal seal (GTMS) welded into an opening in the device housing. A device side of the terminal pins is connected to electronic circuitry housed inside the medical device.

To provide an implantable system, an implantable lead is detachable connected to the header assembly. A typical lead has at least two spaced-apart electrodes which means that the proximal end of the lead has at least two lead contacts that are received in respective header terminal blocks to electrically connect the lead electrodes to the device's electronic circuitry. The electrodes are configured to send electrical pulses to the surrounding body tissue or sense biological signals from the tissue.

While two header terminal blocks is a minimum number for a functioning system, a typical header assembly has a plurality of terminal blocks that are aligned in row oriented perpendicular to a longitudinal axis of the medical device. This means that the medical device must have a lateral width that is sufficient to accommodate the row of terminal blocks. However, there are size limitations to how small the industry can miniaturize such laterally-aligned terminal block configurations using current design technology.

Other efforts to miniaturize AMDs are focused on integrating the active medical device with the lead into a single device. Although this simplifies the connection between the medical device and its pacing/sensing lead, such medical devices cannot be customized according to the physical characteristics of the implantation procedure or the patient's medical condition.

Therefore, there is an ongoing need for an AMD, whether implantable or intended to be worn externally, that is detachably connectable to a lead to provide both stimulation and sensing capability. Desirably, the header assembly has a high density of terminal blocks for connecting the stimulation/sensing lead to the medical device, but in a miniaturized device having a volume that is less than about 3 cc. A smaller medical device is easier to implant in a patient and would be expected to cause less trauma to the patient. A smaller medical device is also expected to be less bothersome to a patient.

SUMMARY OF THE INVENTION

The present invention is directed to a miniaturized active medical device (AMD) that can be either implantable or worn externally. The medical device contains an electrical power source connected to a printed circuit board supporting at least one electronic component. A feedthrough is welded into an opening in the device housing. The feedthrough comprises a ferrule defining a ferrule opening extending to opposed ferrule device side and body fluid side end surfaces. A ceramic insulator is hermetically sealed to the ferrule in a proximal portion of the ferrule opening and extends to an insulator device side residing at or adjacent to the ferrule device side end surface and an insulator body fluid side residing adjacent to the ferrule body fluid side end surface. At least a first via and a second via extend through the ceramic insulator to the insulator device and body fluid sides and a first and second terminal pin are hermetically sealed to the ceramic insulator in the respective vias. The first and second terminal pins each have a device side portion that extends outwardly beyond the device side of the ceramic insulator and is connected to the device electronic circuitry comprising the at least one electronic component supported on the printed circuit board housed inside the medical device, and a body fluid side portion that extends outwardly beyond the body fluid side of the ceramic insulator. The body fluid side portion of the terminal pins provides for electrical connection to a lead.

In the present AMD, the first and second feedthrough terminal pins have different lengths and comprise a shorter terminal pin and a longer terminal pin that are grouped as a pair of terminal pins. The pair of terminal pins are electrically connected to respective in-line terminal blocks housed inside a silicone insulator. In particular, the shorter terminal pin is connected to a proximally-positioned terminal block and the longer terminal pin is connected to a distally-positioned terminal block housed in the silicone insulator. The silicone insulator in turn is housed in a distal portion of the ferrule opening, abutting the hermetically sealed ceramic insulator.

The feedthrough is detachably connected to a lead connector/strain-relief subassembly that is connected to the proximal end of an implantable lead. The lead connector/strain-relief subassembly supports at least one co-axial lead pin. That way, when the lead connector/strain-relief subassembly of the implantable lead is connected to the feedthrough supporting the silicone insulator housing the in-line terminal blocks, the lead electrodes are connected to a respective one of the pair of terminal pins sealed to the ceramic insulator housed inside the ferrule of the feedthrough.

Thus, an advantage of the present AMD in comparison to a conventional medical device is that arranging two terminal pins connected to a pair of in-line terminal blocks that are detachably connected to a co-axial lead pin housed in the lead connector/strain-relief subassembly of the implantable lead represents a reduction in device size without compromising system functionality. Longitudinally aligning the pair of in-line terminal blocks with the co-axial lead pin at the proximal end of the lead enables an AMD according to the present invention to have a higher density of terminal blocks for connecting a stimulation/sensing lead to the medical device than in a conventional device header. Since the terminal blocks are aligned in the axial directions of both the medical device and the lead body, the medical device connected to the lead as an assembly has a relatively shorter lateral width and consequently a smaller volume.

Also, the co-axial lead pin helps to reduce the size of the lead. Desirably, the lead is small enough to pass through a catheter or sheath into an implantation site prior to being connected to the medical device. This provides the physician with greater flexibility in selecting the proper lead length and electrode pattern. In that respect, the present miniaturized AMD enables a physician to match the medical device with a desired lead length and electrode pattern prior to implanting the lead and the AMD.

Accordingly, the purpose of the present inventive subject matter is to reduce the size of an AMD by reducing the volume of the connection between the medical device and its associated lead. Size reduction is realized by reconfiguring connections between the electrical contacts at the proximal end of the lead and the terminal blocks connected to the terminal pins of the feedthrough for the medical device so that the terminal blocks are not aligned perpendicular to the length of the medical device, as is customary. Instead, the device housing has a length extending along a longitudinal axis, and secondary axes of the feedthrough terminal pins paired to a lead connector pin are aligned parallel to the device's longitudinal axis. This connection structure reduces the volume of the lead-to-medical device connection, which helps to reduce the total volume of the implantable AMD system.

These and other aspects of the present invention will become increasingly more apparent to those skilled in the art by reference to the following detailed description and to the appended drawings.

DETAILED DESCRIPTION OF THE PREFERRED EMBODIMENTS

As used herein, the term "active medical device" means a medical device, whether implantable or worn externally, that is designed to deliver electrical stimulation to a patient or sense biological signals from body tissue, or both stimulate and sense.

Figure 1:
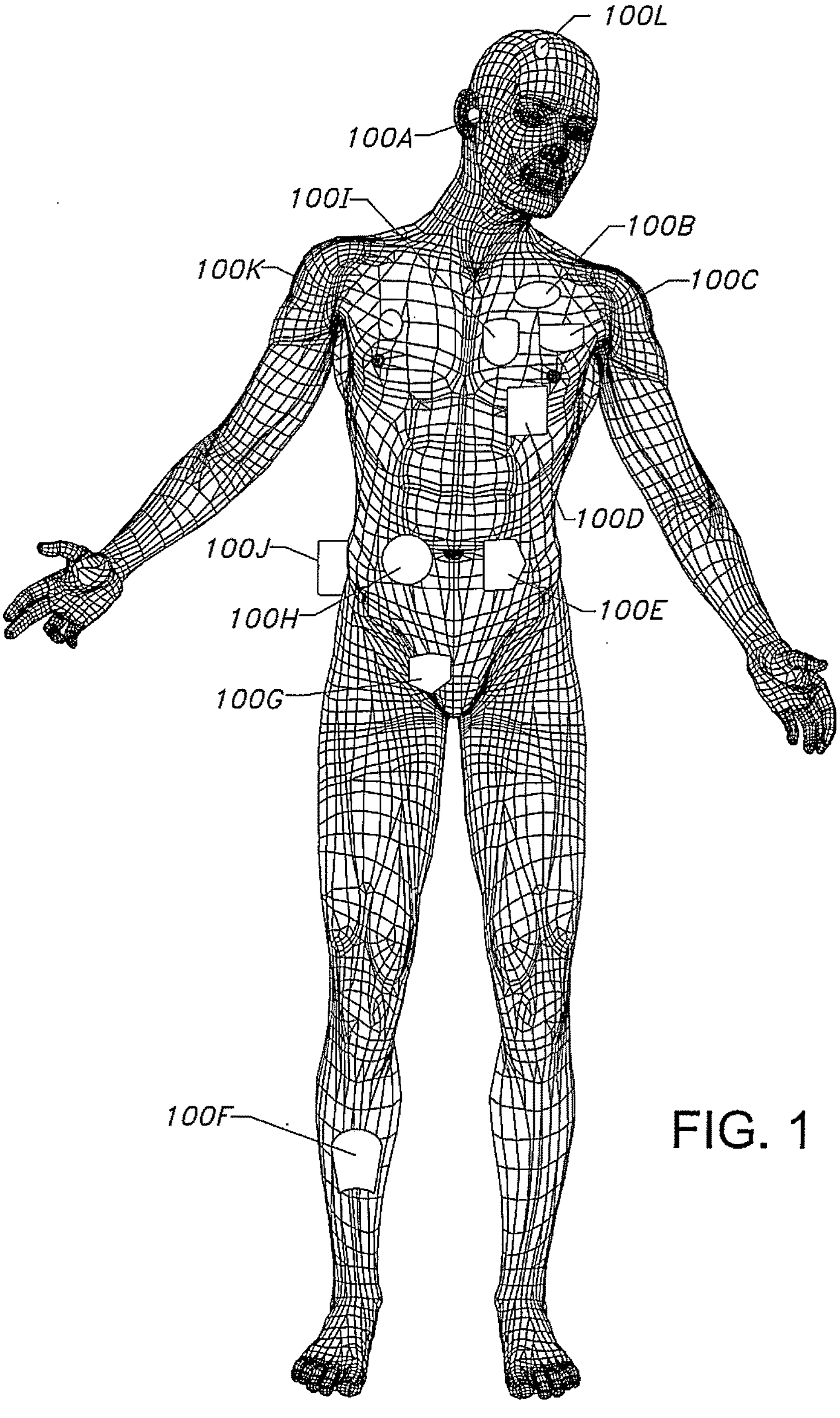
FIG. 1 is a wire formed diagram of a generic human body showing a number of medical devices 100A to 100L according to the present invention that can either be implanted in a patient's body tissue or attached externally to the body.

Turning now to the drawings, FIG. 1 is a wire form diagram of a generic human body illustrating various types of active medical devices according to the present invention that can either be implanted in a patient's body or attached externally to the body.

Numerical designation 100A represents a family of hearing devices which can include the group of cochlear implants, piezoelectric sound bridge transducers, and the like.

Numerical designation 100B represents a variety of neurostimulators, brain stimulators, and sensors. Neurostimulators are used to stimulate the Vagus nerve, for example, to treat epilepsy, obesity, and depression. Brain stimulators are pacemaker-like devices and include electrodes implanted deep into the brain for sensing the onset of a seizure and also for providing electrical stimulation to brain tissue to prevent a seizure from occurring. The lead wires associated with a deep brain stimulator are often placed using real time MRI imaging. Sensors include optical sensors, motion sensors, acoustic sensors, pressure sensors, analyte sensors, and electromagnetic sensors, among others.

Numerical designation 100C shows a cardiac pacemaker which is well-known in the art.

Numerical designation 100D includes the family of left ventricular assist devices (LVADs), and artificial heart devices.

Numerical designation 100E includes a family of drug pumps which can be used for dispensing insulin, chemotherapy drugs, pain medications, and the like.

Numerical designation 100F includes a variety of bone growth stimulators for rapid healing of fractures.

Numerical designation 100G includes urinary incontinence devices.

Numerical designation 100H includes the family of pain relief spinal cord stimulators and anti-tremor stimulators. Numerical designation 100H also includes an entire family of other types of neurostimulators used to block pain.

Numerical designation 100I includes a family of implantable cardioverter defibrillator (ICD) devices and also the family of congestive heart failure devices (CHF). This is also known in the art as cardio resynchronization therapy devices, otherwise known as CRT devices.

Numerical designation 100J illustrates an externally worn pack. This pack could be an external insulin pump, an external drug pump, an external neurostimulator or even a ventricular assist device.

Numerical designation 100K illustrates one of various types of EKG/ECG external skin electrodes which can be placed at various locations on the patient's body.

Numerical designation 100L represents external EEG electrodes that are placed on the patient's head.

Figure 2:
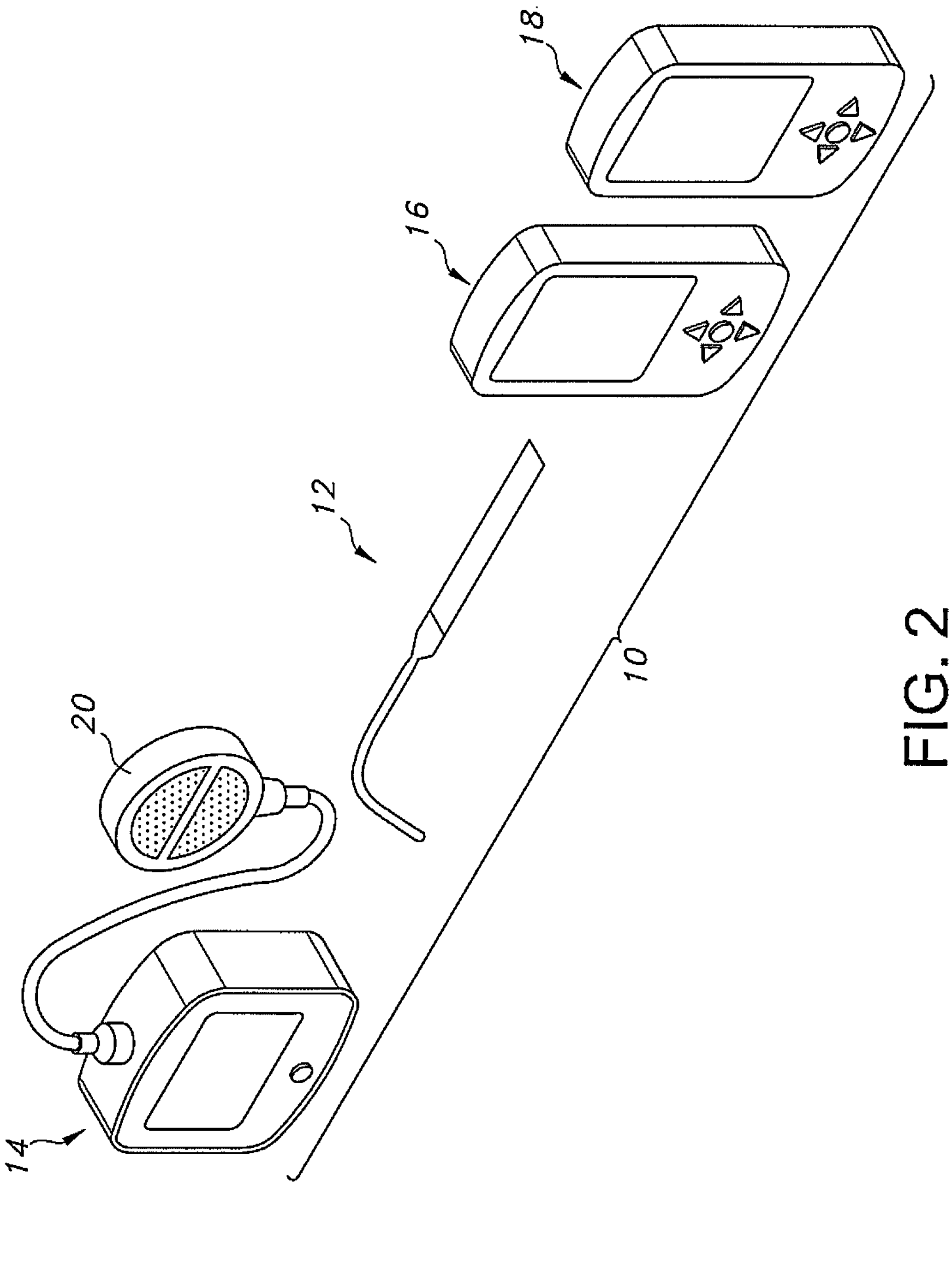
FIG. 2 is a simplified block diagram of an exemplary medical device system 10 according to the present invention.

To provide context to the various medical devices 100A to 100L illustrated in FIG. 1, FIG. 2 illustrates a simplified block diagram of an exemplary medical device system 10 according to the present invention. The medical device system 10 includes an active medical device (AMD) 12, which is any one of various types of the medical devices that include a lead, whether implantable or external, as described above with reference to FIG. 1. The medical device system 10 also has an external charger 14, a patient programmer 16, and a clinician programmer 18.

The patient programmer 16 and the clinician programmer 18 may be portable handheld devices, such as a smartphone or other custom device, that are used to configure the AMD 12 so that the AMD can operate in a desired manner. The patient programmer 16 is used by the patient in whom the AMD 12 is implanted. The patient may adjust the parameters of electrical stimulation delivered by the AMD 12, such as by selecting a stimulation program, changing the amplitude and frequency of the electrical stimulation, among other parameters, and by turning stimulation on and off. Additionally, the patient programmer 16 may collect and display data being collected by the device 12 and alert the patient to potential health risks.

The clinician programmer 18 is used by medical personnel to configure the other system components and to adjust stimulation parameters that the patient is not permitted to control. These include setting up stimulation programs from which the patient may choose and setting upper and lower limits for the patient's adjustments of amplitude, frequency, and other parameters. It is also understood that although FIG. 2 illustrates the patient programmer 16 and the clinician programmer 18 as two separate devices, they may be integrated into a single programmer in some embodiments.

Electrical power can be delivered to the AMD 12 through an external charging pad 20 that is connected to the external charger 14. In some embodiments, the external charging pad 20 is configured to directly power the AMD 12 or it is configured to charge a rechargeable electrical power source (not shown) of the AMD. The external charging pad 20 can be a hand-held device that is connected to the external charger 14, or it can be an internal component of the external charger. The external charger 14 and the charging pad 20 can also be integrated into a single device that is strapped on or attached to the patient with adhesive, and the like.

Figure 3:
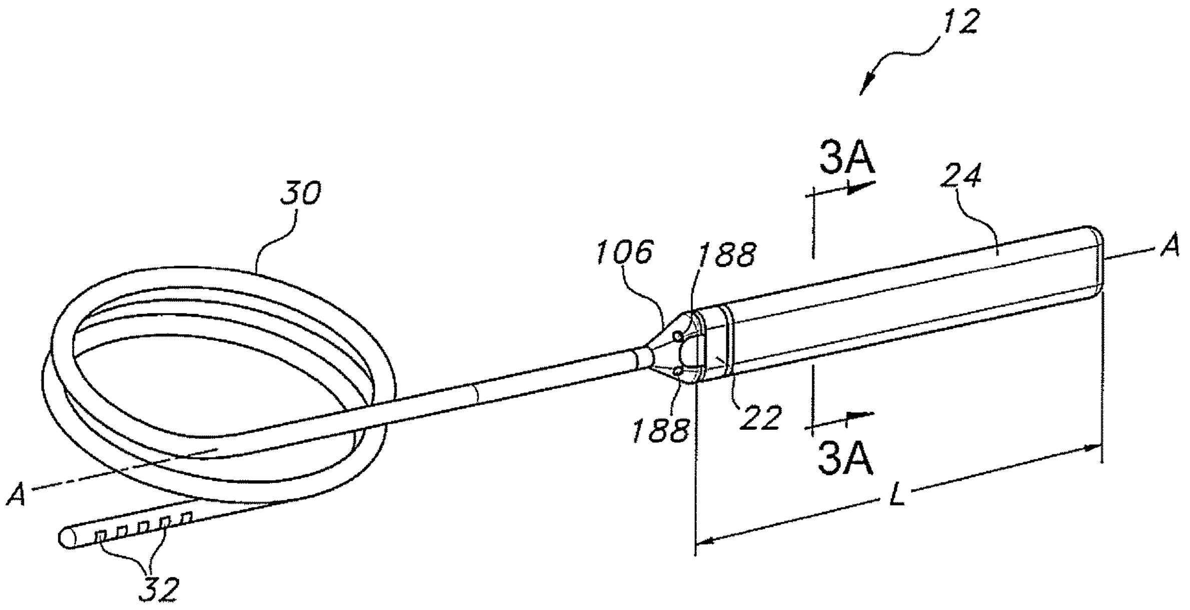
FIG. 3 is a perspective view of a header assembly 22 for an exemplary active implantable medical device (AMD) 12 according to the present invention with the header assembly being detachably connected to an implantable lead 30.
Figure 3A:
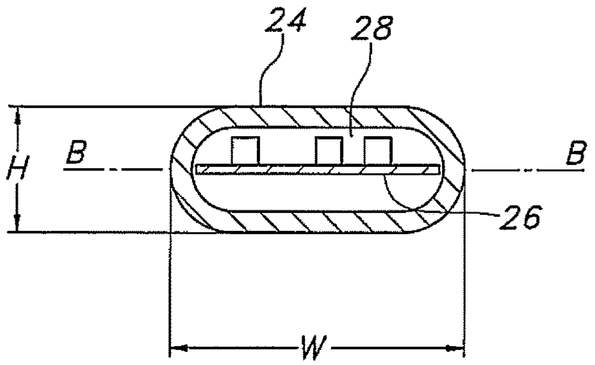
FIG. 3A is a cross-sectional view taken along line 3A-3A of FIG. 3.

Referring now to FIGS. 3 and 3A, these drawings illustrate the AMD 12 as an exemplary embodiment of the various medical devices 100A to 100L illustrated in FIG. 1 and the exemplary AMD 12 shown in the medical device system 10 in FIG. 2 that can be implanted in a patient's body or worn externally on a patient's body. The AMD 12 is shown as an elongate device having a header assembly 22 connected to a housing 24 for the AMD. The device housing 24 has an exemplary length L of about 15 mm extending along a longitudinal axis A-A, a width W of about 7 mm extending along a lateral axis B-B, and a cross-sectional height H of about 3 mm. According to the present invention, however, the shape of the AMD 12 is not limited to the elongate shape that is shown. For example, the AMD 12 could have a cylindrical shape or a shape that is not elongated.

The device housing 24 contains a printed circuit board (PCB) assembly comprising a PCB 26 supporting at least one electronic circuit or electronic component 28. The device housing 24 also contains an electrical power source (not shown) that is electrically connected to the PCB assembly to provide electrical power to the at least one electronic circuit or electronic component 28. The PCB assembly in turn provides electrical power to a lead 30 that is connected to the header assembly 22. The lead 30 has a number of electrodes 32 that are configured to deliver current pulses to the body tissue, receive sensed electrical signals pertaining to functions of a body tissue in which the AMD 12 is implanted, or both sense electrical signals and deliver current pulses. Titanium is a preferred material for the device housing 24.

The electrical power source for the AMD 12 can be a capacitor or a rechargeable battery, for example a hermetically sealed rechargeable Li-ion battery. However, the electrical power source is not limited to any one chemistry or even a rechargeable chemistry and can be of an alkaline cell, a primary lithium cell, a rechargeable lithium-ion cell, a Ni/cadmium cell, a Ni/metal hydride cell, a supercapacitor, a thin film solid-state cell, and the like. Preferably, the electrical power source is a lithium-ion electrochemical cell comprising a carbon-based or $Li_4Ti_5O_{12}$-based anode and a lithium metal oxide-based cathode, such as of $LiCoO_2$ or lithium nickel manganese cobalt oxide ($LiNi_aMn_bCO_{1-a-b}O_2$). The electrical power source can also be a solid-state thin film electrochemical cell having a lithium anode, a metal-oxide based cathode and a solid electrolyte, such as an electrolyte of LiPON ($Li_xPO_yN_z$).

Figure 4:
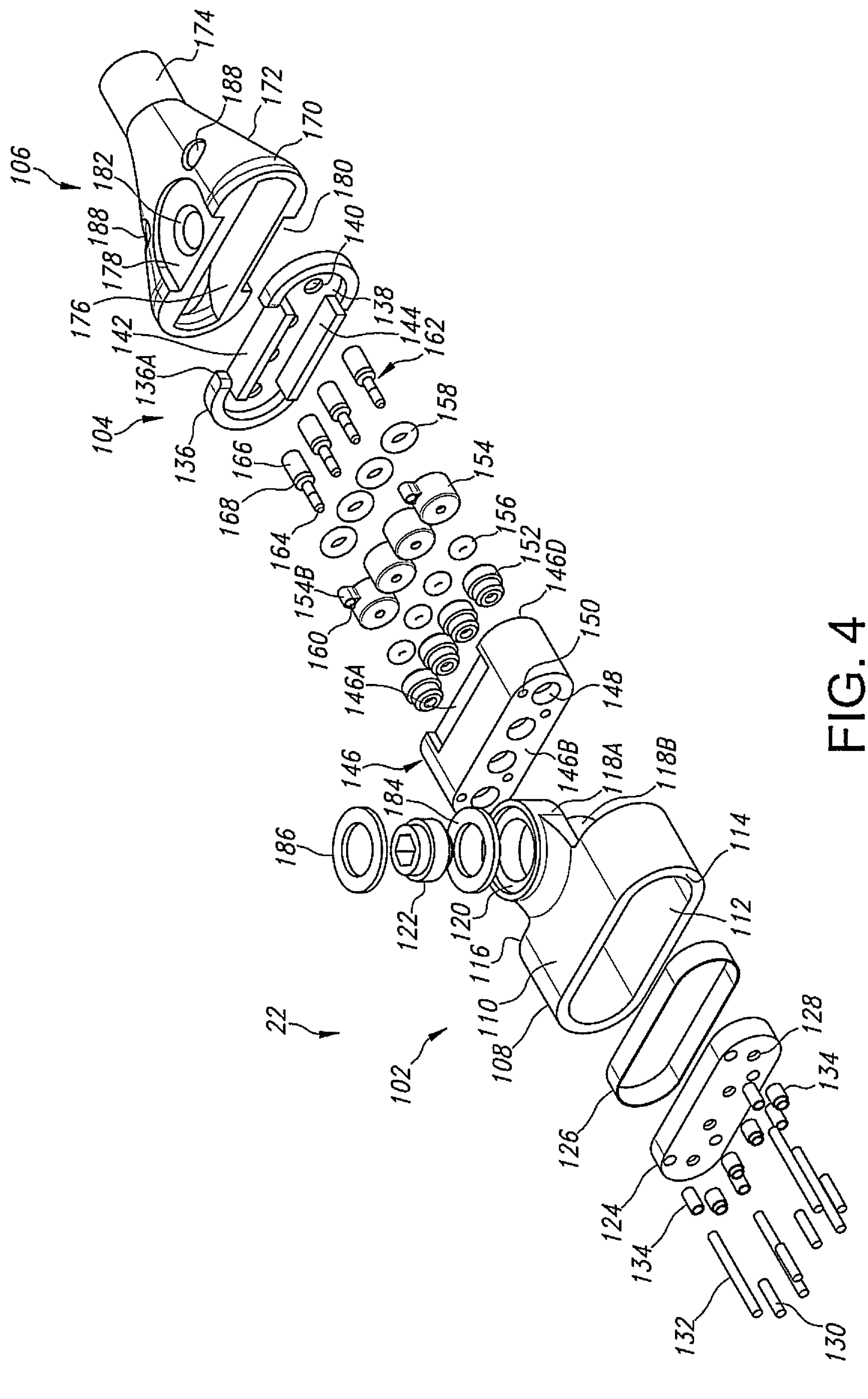
FIG. 4 is an exploded view of the header assembly 22 according to the present invention shown in FIG. 3.
Figure 5:
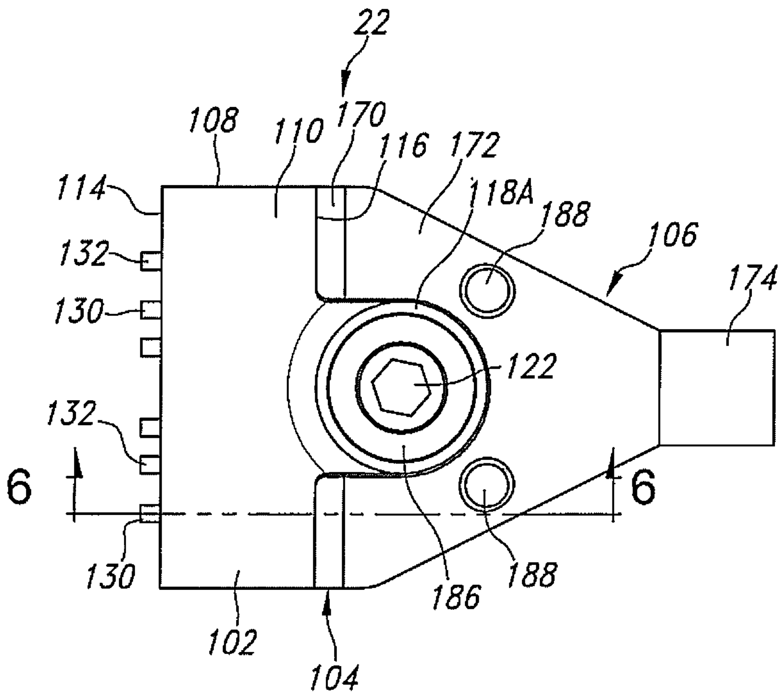
FIG. 5 is a plan view of the header assembly 22 shown in FIG. 4.
Figure 6:
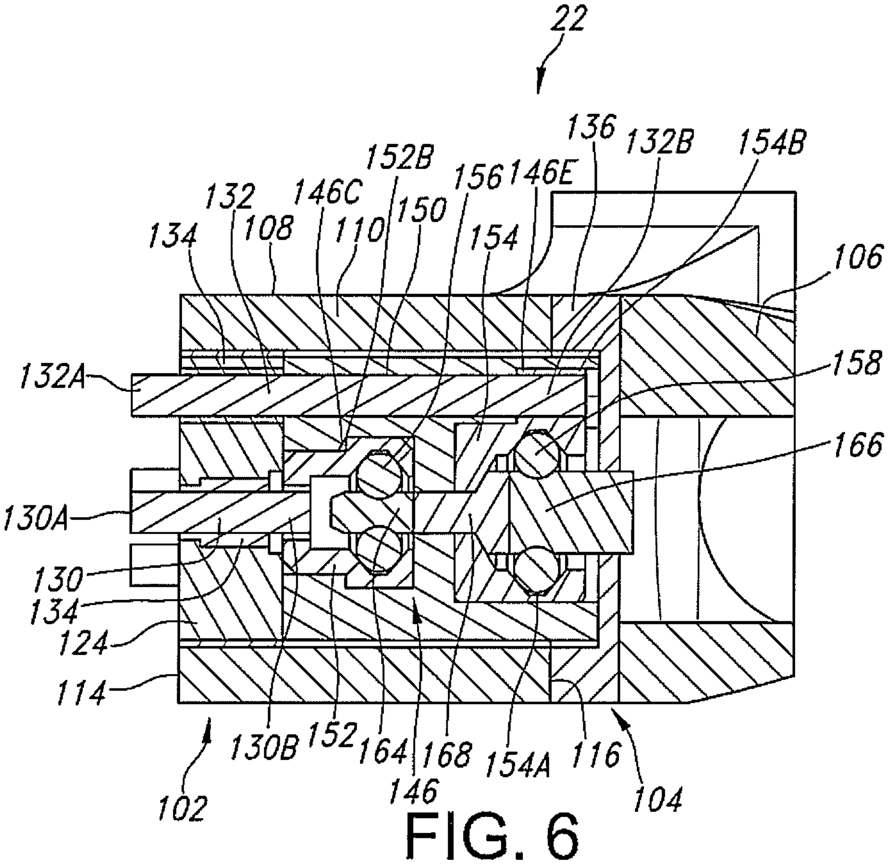
FIG. 6 is a cross-sectional view taken along line 6-6 of FIG. 5.
Figure 7:
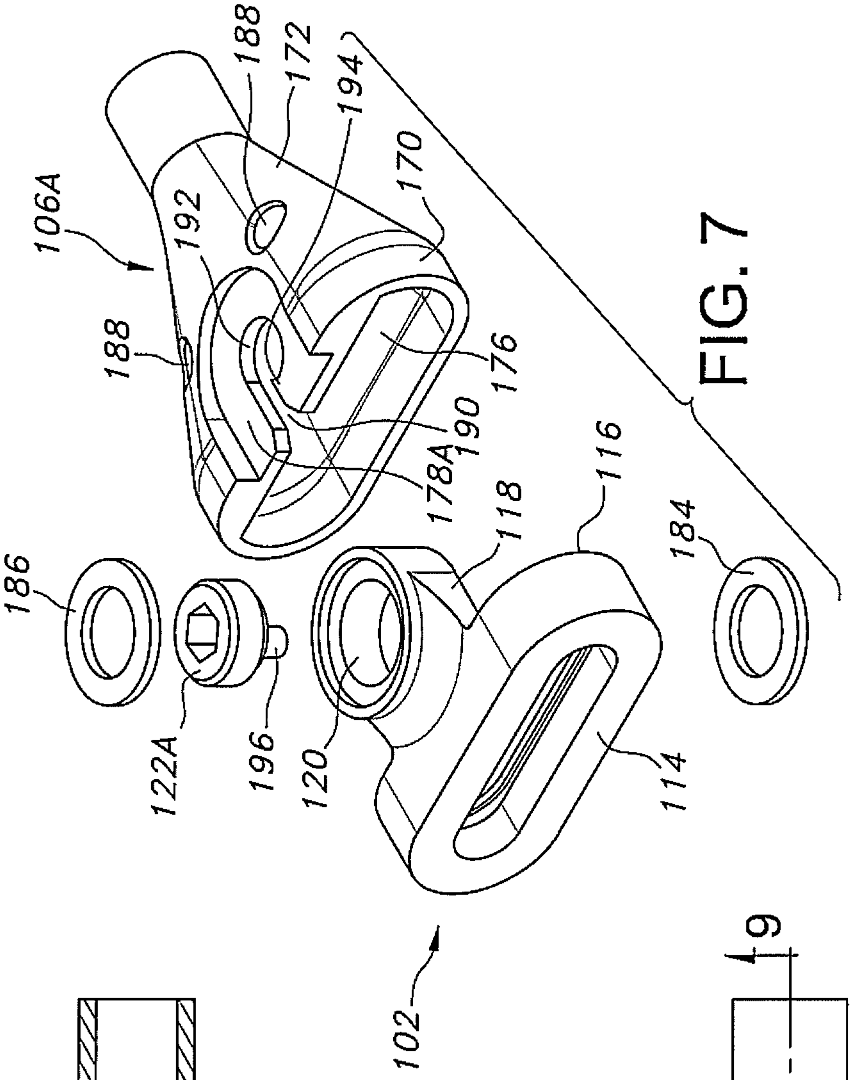
FIG. 7 is an exploded view of an alternate embodiment for connecting the medical device feedthrough 102 for the header assembly 22 to a strain-relief housing 106A connected to the proximal end of the implantable lead 30 shown in FIG. 3.
Figure 9:
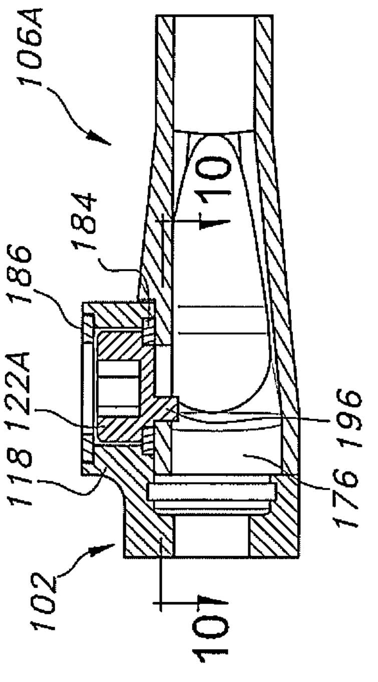
FIG. 9 is a cross-sectional view taken along line 9-9 of FIG. 8.
Figure 8:
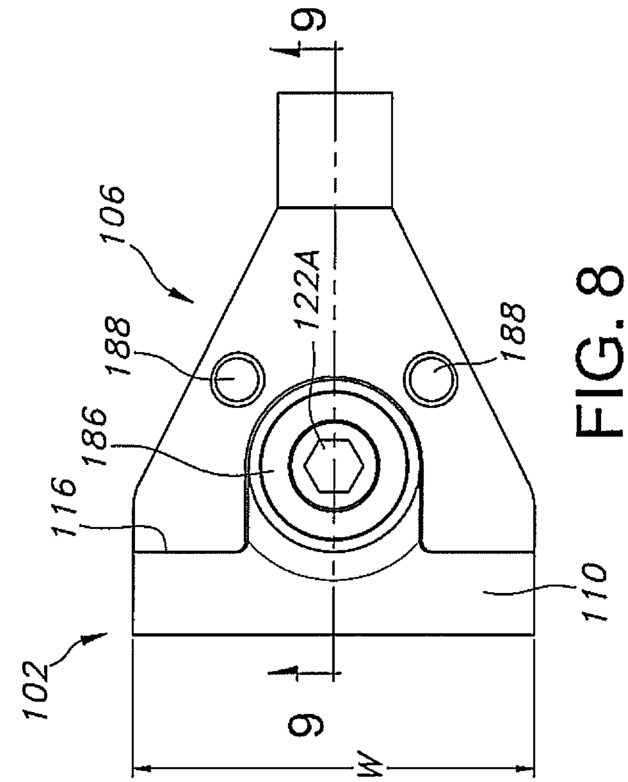
FIG. 8 is a plan view of the feedthrough 102 connected to the strain-relief housing 106A shown in FIG. 7.
Figure 10:
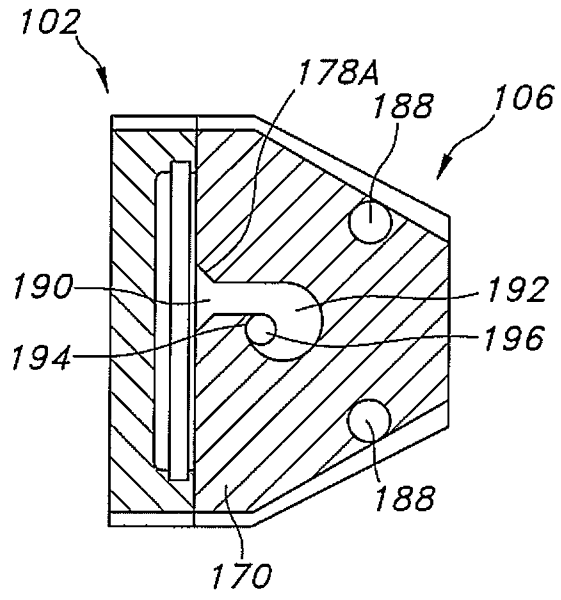
FIG. 10 is a cross-sectional view taken along line 10-10 of FIG. 9.

FIGS. 4 to 6 illustrate an embodiment of the header assembly 22 shown in FIG. 3. The header assembly 22 comprises a feedthrough 102 that is welded into an opening in the housing 24 of the AMD 12. The feedthrough 102 is detachably connected to a lead connector 104 which in turn is connected to a proximal strain-relief housing 106 for the lead 30 shown in FIG. 3. That way, the lead connector 104/strain-relief housing 106 as a subassembly is detachably connectable to the feedthrough 102 for selectively connecting and disconnecting the lead 30 shown in FIG. 3 to and from the AMD 12 through the feedthrough 102.

The feedthrough 102 includes a ferrule 108 having an annular sidewall 110 surrounding an opening 112. The annular sidewall 110 has a length extending from a proximal or device side end surface 114 to a distal or body fluid side end surface 116. Opposed centrally located upper and lower hubs 118A and 118B extend distally from the body fluid side end surface 114 of the annular sidewall 110. The upper hub 118A has an opening 120 that receives a fastener 122, for example, a set screw. The lower hub 118B does not have an opening. The ferrule 108 is preferably made of titanium.

A ceramic insulator 124 resides in a proximal portion of the ferrule opening 112 where the insulator is hermetically sealed to the ferrule 108 with a gold braze 126, as is well known by those skilled in the art of feedthrough assemblies. When the ferrule 104 hermetically sealed to the ceramic insulator 124 is attached to an opening in a housing of the AMD 12, the ferrule and insulator body fluid sides, and the ferrule and insulator device sides reside outside and inside the AMD, respectively. Alumina is a suitable material for the ceramic insulator 124.

The ceramic insulator 124 has a number of vias 128 that extend through its length from a body fluid side to a device side thereof. While eight vias 128 are shown, that is not a limitation of the present invention. There can be less than or more than eight vias, as a particular AMD 12 will require.

Terminal pins 130, 132 reside in a respective one of the vias 128. The terminal pins are provided as a relatively shorter terminal pin 130 paired with a relatively longer terminal pin 132. The terminal pins 130, 132 are hermetically sealed in a respective via 128 using a gold braze pre-form 134, as is well known by those skilled in the art. A longitudinal axis of each of the terminal pins 130, 132 is aligned parallel to the longitudinal axis A-A of the device housing 24 (FIGS. 3 and 3A). Platinum is a suitable material for the terminal pins 130, 132.

The relatively shorter terminal pins 130 are cylindrically-shaped members extending from a proximal or device side portion 130A that is continuous with a distal or body fluid side portion 130B (FIG. 6). With a terminal pin 130 brazed into a via 128 in the ceramic insulator 124, its device side portion 130A extends outwardly beyond the device side of the ceramic insulator 124 and its body fluid side portion 130B extends outwardly beyond the body fluid side of the insulator.

Similarly, the relatively longer terminal pins 132 are cylindrically-shaped members extending from a proximal or device side portion 132A that is continuous with a distal or body fluid side portion 132B (FIG. 6). With a terminal pin 132 brazed into a via 128 in the ceramic insulator 124, its device side portion 132A extends outwardly beyond the device side of the ceramic insulator 124 and its body fluid side portion 132B extends outwardly beyond the body fluid side of the insulator.

As shown in FIGS. 4 and 6, a silicone insulator 146 is housed inside the distal portion of the ferrule 108. The silicone insulator 146 has an upper recess 146A, a lower recess (not shown) and a number of openings that extend through its length from a proximal-facing end surface 146B adjacent to the ceramic insulator 124 to a distal end surface adjacent to the distal or body fluid side end surface 116 of the ferrule 108. The openings comprise a relatively larger diameter opening 148 that is paired with a relatively lesser diameter opening 150. In the exemplary header assembly 22 illustrated in the drawings, there are four pairs of a large diameter opening 148 positioned adjacent to a lesser diameter opening 150.

As shown in FIGS. 4 and 6, the silicone insulator 146 supports a proximal metallic coil spring housing 152 and a distal metallic coil spring housing 154. Titanium is a suitable material for the proximal and distal coil spring housings 152, 154.

The proximal coil spring housing 152 is connected to the distal or body fluid side portion 130B of the shorter terminal pin 130 by a weld (not shown) and comprises an annular recess 152A having a U-shape in cross-section that is sized to receive and retain a relatively lesser-diameter metallic annular coil spring 156. The lesser-diameter coil spring 156 seated in the annular recess 152A of the proximal housing 152 forms a proximal terminal contact or terminal block that is then positioned in a proximal portion of each of the larger diameter openings 148 in the silicone insulator 146. This is done by moving the proximal housing 152 welded to the body fluid side portion 130B of the shorter terminal pin 130 into the opening 148 at the proximal-facing end surface 146B (FIG. 6) of the silicone insulator 146. The silicone insulator 146 is a compliant body with a proximal internal annular ledge 146C that snaps over a similarly sized annular step 152B of the proximal housing 152 for the lesser-diameter annular coil spring 156 to retain this positioning.

The distal coil spring housing 154 comprises an annular recess 154A having a U-shape in cross-section that is sized to receive and retain a relatively larger-diameter metallic annular coil spring 158. The larger-diameter coil spring 158 seated in the annular recess 154A of the distal housing 154 forms a distal terminal contact or terminal block that is then positioned in a distal portion of each of the larger diameter openings 148 in the silicone insulator 146. This is done by moving the distal housing 154/larger-diameter coil spring 158 assembly into the opening 148 at the distal-facing end surface 146D of the silicone insulator 146. Moving the distal housing 154/larger-diameter coil spring 158 assembly into the opening 148 also positions the distal portion of the longer terminal pin 132 in an opening 160 in the upstanding ear 154B of the distal housing 154. The compliant silicone insulator 146 has a distal internal annular ledge 146E that snaps over the distal housing 154 including its upstanding ear 154B to retain this positioning. BAL SEAL® type canted coil springs are suitable for both the lesser-diameter and the larger-diameter annular coil springs 156, 158. BAL SEAL is a registered trademark of Bal Seal Engineering Co., Inc.

The lead connector 104 is an electrically non-conductive member that is made from a polymeric material, for example, PEEK. As shown in FIGS. 4 and 6, the lead connector 104 comprises an oval-shaped annular sidewall 136 extending proximally from a plate-shaped base 138. The oval-shaped annular sidewall 136 has an upper recess 136A that is sized to receive the upper hub 118A and a lower recess (not shown) that is sized to receive the lower hub 118B extending from the ferrule 110 when the feedthrough 102 is connected to the lead connector 104/strain-relief 106 sub-assembly, as will be described in greater detail hereinafter. The lower hub 118B is smaller than the upper hub 118A and serves as a keying feature so that the feedthrough 102 can be connected to the lead connector 104/strain-relief 106 sub-assembly in only one position.

An upper plate-shaped ledge 142 extends proximally from the base plate 138 of the lead connector 104, underneath the upper recess 136A. Symmetrically, a lower plate-shaped ledge 144 extends proximally from the base plate 138, above the lower recess 136B. The upper and lower ledges 142, 144 are parallel to each other and they extend proximally outwardly beyond the oval-shaped annular sidewall 136.

The base plate 138 of the lead connector 104 is provided with a number of openings 140, four are shown, that are aligned side-by-side along a lateral axis that is parallel to the lateral axis B-B shown in FIG. 3A. A co-axial lead pin 162 is supported in each of these openings 140. As shown in FIGS. 4 and 6, the lead pin 162 comprises a center conductor 164 and a circumferential outer conductor 166 that are electrically isolated from each other by an insulating dielectric 168. The outer conductor 166 is received in the opening 140.

The strain-relief housing 106 is a one-piece member made from an electrically non-conductive polymeric material, for example, PEEK, and comprises a proximal annular sidewall 170 that joins to an intermediate annularly bevel-shaped sidewall 172. The beveled sidewall 172 extends distally as it narrows to join a cylindrically-shaped sleeve 174 connected to the proximal end of the lead 30 (FIG. 3). A lumen 176 extends through the strain-relief housing 106.

The strain-relief housing 106 also includes an upper inlet 178 and a lower inlet 180. Both inlets 178, 180 extend inwardly from the proximal annular sidewall 170 into the beveled sidewall 172 and are sized to receive the respective upper and lower hubs 118A and 118B extending distally from the ferrule 108 of the feedthrough 102. The upper inlet 178 has a threaded opening 182, but the lower inlet 180 does not have a threaded opening.

While not shown in the drawings, electrical conductors from the lead 30 extend through the lumen 176 of the strain-relief housing 106 and connect to each of the lead pins 162 in a co-axial connection. This provides electrical continuity from the lead 30 to both the center conductor 164 and the outer conductor 166 of the lead pin 162 supported by the lead connector 104. Then, to form the lead connector 104/strain-relief 106 subassembly, the base plate 138 of the lead connector 104 is butted up and connected to the proximal annular sidewall 170 of the strain-relief housing 106. Since both the lead connector 104 and the strain-relief housing 106 are made from polymeric materials, for example, PEEK, a suitable adhesive is used to make this connection. This connection can also be made by ultrasonic welding the lead connector 104 to the strain-relief housing 106.

With the silicone insulator 146 housed inside a distal portion of the ferrule 108 of the feedthrough 102, an electrical connection is made from the lead 30 to the AMD 12 by plugging the lead pins 162 supported by the base plate 138 of the lead connector 104/stain-relief 106 subassembly into the silicone insulator 146. This movement seats the upper and lower plate-shaped ledges 142, 144 into the respective upper recess 146A and lower recess (not shown) in the silicone insulator 146.

Plugging the lead pins 162 supported by the base plate 138 of the lead connector 104/stain-relief 106 subassembly into the silicone insulator 146 also establishes electrical continuity from the shorter terminal pin 130 to the center conductor 164 of the lead pin 162 contacting the lesser-diameter canted coil spring 156 housed in the metallic proximal housing 152. This means that there is now electrical continuity from the proximal or device side portion 130A of the shorter terminal pin 130 to a conductor (not shown) extending from the lead 30 through the stain-relief housing 106.

Plugging the lead pins 162 into the silicone insulator 146 also establishes electrical continuity from the device side portion 132A of the longer terminal pin 132 to the ear 154B of the metallic distal coil spring housing 154 supporting the canted coil spring 158. The outer conductor 166 of the lead pin 162 is now electrically connected to the canted coil spring 158 seated in the distal coil spring housing 154. This means that there is now electrical continuity from the proximal or device side portion 132A of the longer terminal pin 132 to a conductor (not shown) extending from the lead 30 through the stain-relief housing 106.

To secure these electrical connections, a first retention washer 184 is nested in the opening 120 in the upper ferrule hub 118A. Next, the fastener 122 as a threaded member is moved into the opening 120 in the upper hub 118A. The fastener 122 is then threaded into the threaded opening 182 in the upper inlet 178 of the strain-relief housing 106. A second retention washer 186 is seated on top of the threaded fastener 122.

In contrast, the lower inlet 180 does not have a threaded opening and as previously described, the lower hub 118B is smaller than the upper hub 118A. That way, the lower hub 118B received in the lower inlet 180 serves as a keying feature when connecting the feedthrough 102 to the lead connector 104/strain-relief 106 subassembly.

The strain-relief lumen 176 houses a plurality of electrical conductors of the lead 30 having the lead electrodes 32. The proximal ends of two of the lead electrical conductors are connected to a respective one of the co-axial lead pins 162 supported by the base plate 138 of the lead connector 104. That way, with the strain-relief housing 106 joined to the lead connector 104 and with the lead connector detachable connected to the feedthrough 102, there is electrical continuity from the electronic circuits or components 28 (FIG. 3A) housed inside the AMD 12 to a pair of the terminal pin 130, 132 connected to a respective coil spring 156, 158 housed inside a respective coil spring housing 152, 154 electrically connected to the co-axial lead pin 162 in turn connected to two electrical conductors of the lead 30 connected to two lead electrodes 92. The strain-relief housing 106 is also provided with spaced-apart suture openings 188 that are sized to receive a suture during a medical procedure to secure the header assembly 22 to body tissue, as is well known by those skilled in the art.

FIGS. 7 to 10 illustrate another embodiment for connecting the feedthrough 102 to the lead connector 104/strain-relief 106A subassembly. While the lead connector 104 is not shown in these drawings, that is only for the sake of simplicity. It is understood that a lead connector is an integral part of a header assembly according to the present invention.

The strain-relief housing 106A includes an upper inlet 178A extending inwardly from the proximal annular sidewall 170 into the beveled sidewall 172. However, the inlet 178A has a channel 190 that leads to an off-center spiral cavity 192 ending at a terminal edge 194. The terminal edge 194 is spaced closer to the proximal annular sidewall 170 than the rest of the spiral cavity 192.

In this embodiment, the screw 122A is similar to the treaded member 122 shown in FIGS. 4 and 5 except that it is devoid of threads. Instead, the screw 122A has a depending eccentric pin 196. Moving the screw 122A into the opening 120 in the ferrule hub 118 and into the channel 190 and its spiral cavity 192 causes the eccentric pin 196 to travel along the perimeter of the spiral cavity 192 until it seats at the terminal edge 194. This movement causes the lead connector 102 (not shown in FIGS. 7 to 10) connected to the strain-relief housing 106A to move into an abutting relationship with the body fluid side end surface 116 of the feedthrough 102.

That way, an electrical connection is made from the lead 30 to the AMD 12 by plugging the lead pins 162 supported by the base plate 138 of the lead connector 104/stain-relief 106A subassembly into the silicone insulator 146 housed inside the feedthrough 102. This movement seats the upper and lower plate-shaped ledges 142, 144 into the respective upper recess 146A and lower recess (not shown) in the silicone insulator 146. This movement also establishes electrical continuity from the shorter terminal pin 130 to the center conductor 164 of the lead pin 162 contacting the lesser-diameter canted coil spring 156 housed in the metallic proximal housing 152. This means that there is now electrical continuity from the proximal or device side portion 130A of the shorter terminal pin 130 to a lead conductor (not shown) connected to the center conductor 164 of the lead pin 162.

Plugging the lead pins 162 into the silicone insulator 146 also establishes electrical continuity from the device side portion 132A of the longer terminal pin 132 to the ear 154B of the metallic distal coil spring housing 154 supporting the canted coil spring 158. The outer conductor 166 of the lead pin 162 is now electrically connected to the canted coil spring 158 seated in the distal coil spring housing 154. This means that there is now electrical continuity from the proximal or device side portion 132A of the longer terminal pin 132 to a lead conductor (not shown) connected to the outer conductor 166 of the lead pin 162. Consequently, there is now electrical continuity from the electronic circuits or components 28 (FIG. 3A) supported on the PCB 26 and housed inside the AMD 12 to the terminal pins 130, 132 of the feedthrough 104 connected to the co-axial lead pin 162 connected to the lead 30 and its electrodes 32 (FIG. 3).

Figure 11:
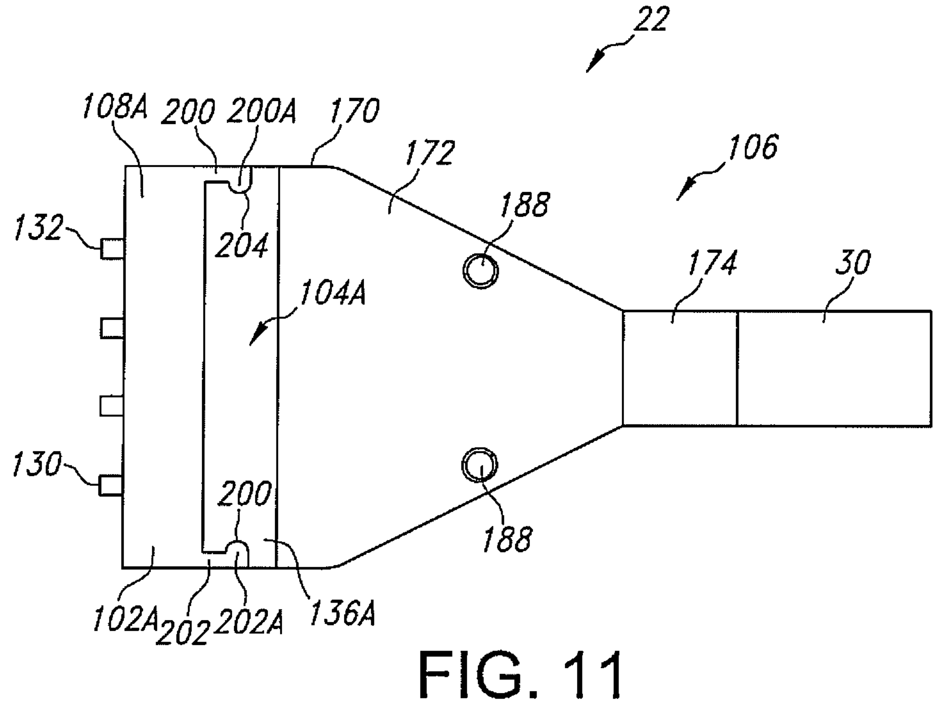
FIG. 11 is a plan view of another embodiment of a header assembly 22 for the AMD 12 shown in FIG. 3.

FIG. 11 illustrates another embodiment of a feedthrough 102A according to the present invention comprising a ferrule 108A having a pair of spaced-apart arms 200 and 202 that extend distally from the body fluid side end surface 116 of the ferrule. The arms 200, 202 are in lieu of the distally-extending hubs 118A, 118B shown in FIGS. 4 and 5 and the hub 118 shown in FIGS. 7 to 9. Instead, the arms 200, 202 are provided with respective inwardly extending detents 200A and 202A. Ferrule 200 is preferably made of titanium.

The lead connector 104A has spaced apart lateral recesses 204 and 206 in its annular sidewall 136A. These recesses 204, 206 receive the detents 200A, 202A of the ferrule extending arms 200, 202 to connect the lead connector 104A to the feedthrough 102A. Since the arms 200, 202 and their respective detents 200A, 202A can be seated and unseated in the recesses 204, 206, this is a detachable connection.

Thus, novel embodiments for a header assembly 22 having the feedthrough 102, 102A of an AMD 12 connected to a lead connector 104, 104A/strain-relief 106, 106A/lead 30 assembly have been described. All embodiments of the lead connector 104, 104A/strain-relief 106, 106A subassembly have a co-axial lead pin 162 that is connected to the proximal end of the implantable lead 30. The center conductor 164 of the co-axial lead pin 162 is then detachably connectable to the shorter length feedthrough terminal pin 130 while the outer conductor 166 of the lead pin 162 is detachably connectable to the longer length feedthrough terminal pin 132. Because the differently-shaped ferrule hubs 118A and 118B extending from the feedthrough 102 can only be mated in the respective inlets 178 and 180 of the strain-relief housing 106 in one direction, detachable connection between the AMD feedthrough 102 and the lead connector 104/strain-relief 106, 106A/lead 30 assembly can only be made in one orientation. The different sizes of the hubs 118A and 118B received in the matching inlets 178 and 180 serves as a keying feature when the feedthrough 102 of the AMD 12 is connected to the lead connector 104/strain-relief 106, 106A subassembly connected to the lead 30. The feedthrough 102 connected to the lead connector 104/strain-relief 106A subassembly shown in FIGS. 7 to 10 can also be connected in only one direction, which is a keying feature.

Moreover, since the terminal blocks 152, 154 connected to a pair of the shorter and longer length terminal pins 130, 132 inside the silicone insulator 146 of the feedthrough 102 are aligned in the axial directions of both the medical device 12 and the lead body 30 connected to the co-axial lead pins 162, the medical device has a relatively shorter lateral width and, if desired, can be manufactured with a volume that is less than about 3 cc. A smaller medical device is easier to implant in a patient and would be expected to cause less trauma to the patient. A smaller medical device is also expected to be less bothersome to a patient.

It is appreciated that various modifications to the inventive concepts described herein may be apparent to those skilled in the art without departing from the spirit and scope of the present invention as defined by the hereinafter appended claims.

What is claimed is:

1. An active medical device (AMD), comprising:

a) a device housing containing an electrical power source connected to a printed circuit board supporting at least one electronic component;

b) a feedthrough welded into an opening in the device housing, the feedthrough comprising:

i) a ferrule defining a ferrule opening extending to a ferrule device side end surface and a ferrule body fluid side end surface;

ii) a ceramic insulator hermetically sealed to the ferrule in a proximal portion of the ferrule opening, the ceramic insulator extending to a ceramic insulator device side residing at or adjacent to the ferrule device side end surface spaced from a ceramic insulator body fluid side; and iii) at least a first, shorter terminal pin and a second, longer terminal pin extending through the ceramic insulator to the ceramic insulator device and body fluid sides, wherein the first shorter and the second longer terminal pins each have a device side portion and a body fluid side portion extending outwardly beyond the respective device and body fluid sides of the ceramic insulator; and c) a silicone insulator housed in a distal portion of the ferrule opening, the silicone insulator comprising:

i) a silicone insulator device side residing adjacent to the ceramic insulator body fluid side and a silicone insulator body fluid side residing at or adjacent to the ferrule body fluid side end surface;

ii) a first opening and a second opening extending to the silicone insulator device and body fluid sides, wherein a distal portion of the first shorter terminal pin resides in the first opening in the silicone insulator and the second longer terminal pin extends through the second opening to the silicone insulator body fluid side;

iii) a proximal metallic housing connected to the distal portion of the first shorter terminal pin and residing in the first opening in the silicone insulator;

iv) a distal metallic housing connected to the distal portion of the second longer terminal pin and residing in the second opening in the silicone insulator, wherein the proximal and distal metallic housings are co-axially aligned in the silicone insulator; and v) a first annular spring and a second annular spring nested in the respective proximal and distal metallic housings;

d) a lead connector, comprising:

i) an annular connector sidewall extending from a connector device side end surface to a connector body fluid side end surface, wherein a base plate connected to an inner surface of the annular connector sidewall has at least a first connector opening; and ii) a co-axial lead pin supported in the first connector opening of the connector base plate, wherein the lead pin comprises a center conductor and an electrically isolated circumferential outer conductor; and e) a lead comprising at least two electrical conductors connected to respective first and second distal electrodes; and f) a strain-relief fixedly connected to the connector body fluid side end surface, wherein the at least two electrical conductors of the lead extend through the strain-relief and are connected to the respective center and circumferential outer conductors of the lead pin supported by the base plate of the connector, g) wherein the ferrule of the feedthrough is connectable to the lead connector connected to the strain-relief so that:

i) the device side portions of the first shorter and the second longer terminal pins of the feedthrough are electrically connected to the at least one electronic component contained in the device housing;

ii) the body fluid side portions of the first shorter and the second longer terminal pins are electrically connected to the respective proximal and distal metallic housings and the respective nested first and second annular springs; and iii) the center and circumferential outer conductors of the co-axial lead pin supported by the lead connector are electrically connected to the respective first and second annular springs nested in the respective proximal and distal metallic housings and to the first and second electrodes of the lead.

2. The AMD of claim 1, wherein the device housing has a length extending along a longitudinal axis, and wherein the first shorter and the second longer terminal pins connected to the respective first and second metallic housings nesting the first and second annular springs are aligned parallel to the longitudinal axis.

3. The AMD of claim 1, wherein the distal metallic housing has an upstanding ear, and the body fluid side portion of the second longer terminal pin is electrically connected to the ear of the distal metallic housing nesting the second annular spring.

4. The AMD of claim 1, wherein the upstanding ear of the distal metallic housing has an opening that receives the body fluid side portion of the second longer terminal pin.

5. The AMD of claim 1, wherein the silicone insulator device side abuts the ceramic insulator body fluid side inside the ferrule opening.

6. The AMD of claim 1, wherein the lead is configured to at least one of deliver electrical stimulation to body tissue or sense biological signals from body tissue.

7. The AMD of claim 1, wherein a hub extends distally from the ferrule, the ferrule hub having a hub opening, and wherein the strain-relief has an inlet with an inlet opening, and wherein with the ferrule hub received in the strain-relief inlet, a fastener received in the ferrule hub opening and the strain-relief inlet opening connects the feedthrough to the lead connector connected to the lead.

8. The AMD of claim 7, wherein the strain-relief inlet opening is threaded, and the fastener received in the ferrule hub opening and the strain-relief inlet opening is a threaded fastener that threadingly mates with the threaded inlet opening.

9. The AMD of claim 7, wherein the annular sidewall of the lead connector has a recess through which extends the ferrule hub received in the strain-relief inlet.

10. The AMD of claim 7, wherein the strain-relief has an inlet and a channel that extend inwardly from a proximal annular sidewall, and wherein the channel leads to an off-center spiral cavity terminating at an edge that is spaced closer to the proximal annular sidewall than the rest of the spiral cavity, and wherein the fastener has a depending eccentric pin so that screwing the fastener into the hub opening and into the strain-relief channel causes the eccentric pin to travel along the perimeter of the spiral cavity until the pin seats at the terminating edge of the spiral cavity to secure the medical device to the lead connector and the strain-relief connected to the lead.

11. The AMD of claim 1, wherein a pair of first and second spaced-apart arms extend distally from the body fluid side end surface of the ferrule, the first and second arms being provided with inwardly extending detents, and wherein first and second lateral recesses are provided in the annular connector sidewall so that with the first and second detents of the first and second spaced-apart extending arms of the ferrule of the feedthrough received in the first and second lateral recesses of the lead connector, the feedthrough is detachably connected to the lead connector connected to the strain-relief.

12. An assembly, comprising:

a) a feedthrough, comprising:

i) a ferrule defining a ferrule opening extending to a ferrule device side end surface and a ferrule body fluid side end surface;

ii) a ceramic insulator hermetically sealed to the ferrule in a proximal portion of the ferrule opening, the ceramic insulator extending to a ceramic insulator device side residing at or adjacent to the ferrule device side end surface spaced from a ceramic insulator body fluid side; and iii) at least a first, shorter terminal pin and a second, longer terminal pin extending through the ceramic insulator to the ceramic insulator device and body fluid sides, wherein the first shorter and the second longer terminal pins each have a device side portion and a body fluid side portion extending outwardly beyond the respective device and body fluid sides of the ceramic insulator; and c) a silicone insulator housed in a distal portion of the ferrule opening, the silicone insulator comprising:

i) a silicone insulator device side residing adjacent to the ceramic insulator body fluid side and a silicone insulator body fluid side residing at or adjacent to the ferrule body fluid side end surface;

ii) a first opening and a second opening extending to the silicone insulator device and body fluid sides, wherein a distal portion of the first shorter terminal pin resides in the first opening in the silicone insulator and the second longer terminal pin extends through the second opening to the silicone insulator body fluid side;

iii) a proximal metallic housing connected to the distal portion of the first shorter terminal pin and residing in the first opening in the silicone insulator;

iv) a distal metallic housing connected to the distal portion of the second longer terminal pin and residing in the second opening in the silicone insulator, wherein the proximal and distal metallic housings are co-axially aligned in the silicone insulator; and v) a first annular spring and a second annular spring nested in the respective proximal and distal metallic housings;

d) a lead connector, comprising:

i) an annular connector sidewall extending from a connector device side end surface to a connector body fluid side end surface, wherein a base plate connected to an inner surface of the annular connector sidewall has at least a first connector opening; and ii) a co-axial lead pin supported in the first connector opening of the connector base plate, wherein the lead pin comprises a center conductor and an electrically isolated circumferential outer conductor; and e) a lead comprising at least two electrical conductors connected to respective first and second distal electrodes; and f) a strain-relief fixedly connected to the connector body fluid side end surface, wherein the at least two electrical conductors of the lead extend through the strain-relief and are connected to the respective center and circumferential outer conductors of the lead pin supported by the base plate of the connector, g) wherein the ferrule of the feedthrough is connectable to the lead connector connected to the strain-relief so that:

i) the body fluid side portions of the first shorter and the second longer terminal pins of the feedthrough are electrically connected to the respective proximal and distal metallic housings and the respective nested first and second annular springs; and ii) the center and circumferential outer conductors of the co-axial lead pin supported by the lead connector are electrically connected to the respective first and second annular springs nested in the respective proximal and distal metallic housings residing in the respective first and second openings in the silicone insulator housed inside the ferrule.

13. The assembly of claim 12, wherein the distal metallic housing has an upstanding ear, and the body fluid side portion of the second longer terminal pin is electrically connected to the ear of the distal metallic housing nesting the second annular spring.

14. The assembly of claim 12, wherein the upstanding ear of the distal metallic housing has an opening that receives the body fluid side portion of the second longer terminal pin.

15. The assembly of claim 12, wherein the silicone insulator device side abuts the ceramic insulator body fluid side inside the ferrule opening.

16. The assembly of claim 12, wherein a hub extends distally from the ferrule, the ferrule hub having a hub opening, and wherein the strain-relief has an inlet with an inlet opening, and wherein with the ferrule hub received in the strain-relief inlet, a fastener received in the ferrule hub and the strain-relief inlet openings connects the feedthrough to the lead connector connected to the lead.

17. The assembly of claim 16, wherein the strain-relief inlet opening is threaded, and the fastener is a threaded fastener that is received in the ferrule hub and the strain-relief inlet openings to threadingly mate with the threaded inlet opening.

18. The assembly of claim 16, wherein the annular sidewall of the lead connector has a recess through which extends the ferrule hub received in the strain-relief inlet.

19. The assembly of claim 16, wherein the strain-relief has an inlet and a channel that extend inwardly from a proximal annular sidewall, and wherein the channel leads to an off-center spiral cavity terminating at an edge that is spaced closer to the proximal annular sidewall than the rest of the spiral cavity, and wherein the fastener has a depending eccentric pin so that screwing the fastener into the hub opening and into the channel and its spiral cavity in the strain-relief causes the eccentric pin to travel along the perimeter of the spiral cavity until it seats at the terminating edge to secure the feedthrough to the lead connector connected to the strain-relief.

20. The assembly of claim 12, wherein a pair of first and second spaced-apart arms extend distally from the body fluid side end surface of the ferrule, the first and second arms being provided with inwardly extending detents, and wherein first and second lateral recesses are provided in the annular connector sidewall so that with the first and second detents of the first and second spaced-apart extending arms of the ferrule of the feedthrough received in the first and second lateral recesses of the lead connector, the feedthrough is detachably connected to the lead connector connected to the strain-relief.

* * * * *